(12) United States Patent
Jia et al.

(10) Patent No.: US 12,203,864 B2
(45) Date of Patent: Jan. 21, 2025

(54) SPARK SPECTROMETRY FOR INCLUSIONS CONTENT DISTRIBUTION ON THE SURFACE OF LARGE SIZE METALLIC MATERIALS (71) Applicant: NCS Testing Technology CO.,LTD, Beijing (CN)

(72) Inventors: Yunhai Jia, Beijing (CN); Liang Sheng, Beijing (CN); Liangjing Yuan, Beijing (CN); Lei Yu, Beijing (CN); Qiaochu Zhang, Beijing (CN)

(73) Assignee: NCS Testing Technology CO., LTD, Beijing (CN)

( * ) Notice: Subject to any disclaimer, the term of this patent is extended or adjusted under 35 U.S.C. 154(b) by 167 days.

(21) Appl. No.: 18/082,822

(22) Filed: Dec. 16, 2022

(65) Prior Publication Data
US 2024/0159680 A1 May 16, 2024

(51) Int. Cl.
G01N 21/67 (2006.01)
G01J 3/06 (2006.01)
G01J 3/457 (2006.01)
G01N 21/31 (2006.01)
G01N 21/88 (2006.01)
G01N 21/93 (2006.01)
G01N 33/2022 (2019.01)

(52) U.S. Cl.
CPC ............... G01N 21/67 (2013.01); G01J 3/06 (2013.01); G01J 3/457 (2013.01); G01N 21/31 (2013.01); G01N 21/8851 (2013.01); G01N 21/93 (2013.01); G01N 33/2022 (2019.01); G01J 2003/061 (2013.01); G01N 2021/3196 (2013.01)

(58) Field of Classification Search
CPC ............... G01N 21/67; G01N 21/8851; G01N 33/2022; G01J 3/457
See application file for complete search history.

(56) References Cited

PUBLICATIONS

Pablo Huazano-Estrada, "Characterization of Inclusion Size Distributions in Steel Wire Rods", Nov. 2022 (Year: 2022).*
Heinz-Martin Kuss, "Comparison of spark OES methods for analysis of inclusions in iron base matters", Feb. 1, 2002 (Year: 2002).*

(Continued)

Primary Examiner — Maurice C Smith (57) ABSTRACT

A spark spectrometry for inclusions content distribution on the surface of large size metallic materials, comprising the following steps: analyzing the surface of large-size metallic materials by spark discharge continuous excitation scanning, obtaining a mixture intensity distribution data of the solid solution and inclusions of an element on the surface of the large-size metallic materials; the relative frequency distribution diagram of spectral intensity is subjected to peak fitting of normal distribution and Gumbel distribution, obtaining an extreme value distribution data of spectral intensity of the inclusions; a size information of the inclusions in a small sample and that of the largest inclusions are correlated with the spectral intensity distribution data of inclusions, obtaining a result of content distribution of the inclusions on the surface of the large size metallic materials. The invention can quickly obtain accurate distribution information of inclusions of various elements on the surface of metallic materials.

7 Claims, 4 Drawing Sheets (56) References Cited

PUBLICATIONS

D. N. Bocka, "Determination of Nonmetallic Inclusions in Metal Alloys by the Method of Spark Atomic Emission Spectroscopy", 2019 (Year: 2019).*

Hongying Du, "Characterization of Nonmetallic Inclusions in Low-Alloyed Steels Using Pulse Distribution Analysis Optical Emission Spectroscopy and Offline Investigation Methods", 2021 (Year: 2021).*

* cited by examiner

Summarizing the mixture intensity distribution data of the solid solution of element and it's inclusions, obtaining a spectral intensity relative frequency distribution diagram of the solid solution of element and it's inclusions.

↓

Analyzing the surface of large-size metallic materials by spark discharge continuous excitation scanning, obtaining a mixture intensity distribution data of a solid solution of element and it's inclusions on the surface of the large size metallic materials.

↓

Fitting the spectral intensity relative frequency distribution diagram to obtain a spectral intensity distribution data of the inclusions.

↓

Taking a sample with a set area on the surface of the large size metallic material as a small sample, and obtaining quantity and size information of the inclusions in the small sample.

↓

Correlating the size information of the inclusions in the small sample with the spectral intensity distribution data of the inclusions; determining a corresponding relationship between the size of the inclusions and the spectral intensity, obtaining a result of content distribution of the inclusions on the surface of the large size metallic materials.

SPARK SPECTROMETRY FOR INCLUSIONS CONTENT DISTRIBUTION ON THE SURFACE OF LARGE SIZE METALLIC MATERIALS

TECHNICAL FIELD

This invention relates to the technical field of surface characterization of metallic materials, particularly relates to a spark spectrometry for inclusions content distribution on the surface of large size metallic materials.

BACKGROUND

Global characterization of inclusions on the surface of large size metallic materials is a difficult and extremely complex technology. The conventional analysis methods for characterizing inclusions in materials, including metallographic method and scanning electron microscope method, usually only aim at the test area below 200 mm², they can't directly characterize inclusions in large size samples. Large metal sample electrolysis method can analyze inclusions larger than 50 μm in 100 mm size metal samples, and the complicated process of this method takes more than 2 weeks, so it can't be used as a conventional and convenient way to characterize inclusions in large size materials; extreme value method, as an indirect method to test inclusions in large size metallic samples, can only infer the information of the largest inclusions, rather than giving the content distribution of inclusions. In addition, some spectral analysis methods can characterize the inclusions and their distribution information on the surface of metal materials by using a rough method that is greater than the threshold intensity to separate an intensity signal of elements of inclusions, but such method cannot strictly determine the actual relative frequency distribution of inclusions intensity signal, wherein, the smaller inclusions signals are considered as a solid solution of elements, while a larger solid solution of elements is considered as the inclusions signal.

SUMMARY

This invention provides a spark spectrometry for inclusions content distribution on the surface of large size metallic materials. This invention correlates a size information under scanning electron microscope with inclusions signal data of spark spectrum analysis of large size metal samples to determine the relationship between the size and intensity of inclusions, thus obtaining the content distribution information of inclusions in large size sample, and solving the problem of content distribution analysis of inclusions on the surface of large size metallic materials.

A spark spectrometry for inclusions content distribution on the surface of large size metallic materials, comprising the following steps:
  analyzing the surface of large-size metallic materials by spark discharge continuous excitation scanning, obtaining a mixture intensity distribution data of a solid solution of elements and inclusions on the surface of the large size metallic materials;
  summarizing the mixture intensity distribution data of the solid solution of element and it' inclusions, obtaining a spectral intensity relative frequency distribution diagram of the solid solution and the inclusions of element;
  fitting the spectral intensity relative frequency distribution diagram to obtain a spectral intensity distribution data of the inclusions;
  taking a sample with a pre-set area on the surface of the large size metallic material as a small sample, and obtaining quantity and a size information of the inclusions in the small sample;
  correlating the size information of the inclusions in the small sample with the spectral intensity distribution data of the inclusions; determining a corresponding relationship between the size of the inclusions and the spectral intensity, obtaining a result of content distribution of the inclusions on the surface of the large size metallic materials.

Further, the step of analyzing the surface of the large size metallic materials by the spark discharge continuous excitation scanning, obtaining the mixture intensity distribution data of solid solution of element and it's inclusions on the surface of the large size metallic materials, comprising processes as follows:
  First, placing a scanning probe at the leftmost position of the upper end of the large size metallic materials in the Y direction, and carrying out spark discharge scanning from left to right along the X direction, after scanning the first line, placing the scanning probe at the leftmost position of the second line at the upper end of the large size metallic materials in Y direction, next, completing the second line of scanning from left to right until all the lines of the large size metallic materials are scanned from top to bottom, obtaining the mixture intensity distribution data of solid solution of element and it's inclusions on the surface of the large size metallic materials.

Further, the step of fitting the spectral intensity relative frequency distribution diagram to obtain the spectral intensity distribution data of the inclusions, comprising processes as follows:
  carrying out peak fitting processing on the spectral intensity relative frequency distribution diagram by normal distribution and Gumbel distribution to obtain the normal distribution diagram of the solid solution part of the left main peak and the Gumbel distribution diagram of the inclusions of the right peak tailing.

Obtaining the spectral intensity distribution data of the inclusions based on the Gumbel distribution diagram of the inclusions at the right peak tailing.

Further, the step of taking the sample with the pre-set area on the surface of the large size metallic materials as the small sample, comprising processes as follows:
  Obtaining the area of the surface of the large size metallic materials, which is expressed as $S_{large}$; obtaining the pre-set area of the small sample, which is expressed as $S_{small}$; the surface area of large size metallic materials and the pre-set area of the small sample, satisfying the following relationship:

$$T = S_{large}/S_{small}$$

Wherein, T is within the range of 100~10000.

Further, the step of taking the sample with the pre-set area on the surface of the large size metallic materials as the small sample, and obtaining the quantity and size information of the inclusions in the small sample, comprising processes as follows:
  Cutting a small sample with a pre-set area about 160~200 mm² from the surface of a large size metallic materials, grinding and polishing this small sample, placing the small sample under a scanning electron microscope, and identifying and quantitatively detecting inclusions larger than 1 μm on the surface of the small sample, at the same time, aluminum foil is introduced to the edge of the small sample to correct the gray threshold of the electron microscope picture, confirming the recognition brightness threshold of the inclusions. When the brightness of the particles observed by scanning electron microscope is less than the brightness threshold, the particles are judged as inclusions, and the energy spectrum analysis is carried out to record and save a quantity and size information of inclusions, and the quantity and size information of the largest inclusions is recorded as the first data.

Further, again, taking a sample with a pre-set area on the surface of the large size metallic materials, re-preparing the sample, grinding and polishing the re-prepared sample to obtain a small sample, and placing it under a scanning electron microscope again to obtain a size information of the largest inclusions, and recording it as the second data; repeating the same process described in the previous sentence, in order to obtain the size information of the largest inclusions and record it as the third data; repeating the same process until 24 groups of data are recorded; based on the extreme value analysis, calculating the size of the largest inclusions formed by inclusions elements on the surface of the large size metallic materials, the calculated size corresponds to the maximum intensity signal in the spectral intensity distribution data of inclusions.

Further, the step of correlating the size information of the inclusions in the small sample with the spectral intensity distribution data of the inclusions; determining the corresponding relationship between the size of inclusions and spectral intensity, obtaining the result of content distribution of the inclusions on the surface of large size metallic materials, comprising processes as follows:

classifying and counting the size information of the inclusions under a scanning electron microscope, obtaining a statistical frequency of each class with a class interval of 2 μm;

the spectral intensity distribution data of the inclusions are divided into the same class based on the statistical frequency of the 2 μm class interval under scanning electron microscope, obtaining the average size and average intensity of each class;

drawing a calibration curve of areas of intensity according to the relationship of the average intensity and the maximum intensity of the each class with the average size and maximum size of the inclusions obtained under the class frequency process;

according to a calibration curve of areas of intensity, converting the intensity-relative frequency spectrum into a size-frequency spectrum of the inclusions, multiplying the size-frequency spectrum of the inclusions with the total number of spectral intensities of the elements of inclusions to obtain the inclusions size distribution graph, setting the class interval to distinguish each class, thus obtaining the result of inclusions content distribution.

This invention provides the spark spectrometry for inclusions content distribution on the surface of large size metallic materials, using spark spectrometry on the surface of large size metallic materials to obtain the spectral intensity signal data of inclusions in a large-size range, and fitting the spectral intensity relative frequency distribution diagram to separate the solid solution intensity signal of elements from the intensity signal of inclusions, obtaining the inclusion intensity distribution diagram, thus realizing the separation of the inclusion intensity signals from the solid solution signals of elements; based on the analysis of small samples in the same large-size metal material by scanning electron microscope, the size information of inclusions under scanning electron microscope is correlated with the intensity distribution of inclusions in large-size metal materials scanned by spark spectrometry, determining the corresponding relationship between the size and intensity of inclusions, so as to obtain the size distribution information of inclusions in large-size metal samples.

BRIEF DESCRIPTION OF DRAWINGS

In order to more clearly explain the embodiments of the present invention or the technical solutions in the prior art, the following will briefly introduce the drawings that need to be used in the embodiments. Obviously, the drawings in the following description are only some embodiments of the present invention. For those of ordinary skill in the art, other drawings can be obtained according to these drawings without any creative labor.

DETAILED DESCRIPTION OF EMBODIMENTS

The technical solutions in the embodiments of the present invention will be clearly and completely described below with reference to the drawings in the embodiments of the present invention. Obviously, the described embodiments are only part of the embodiments of the present invention, but not all of them. Based on the embodiment of the present invention, all other embodiments obtained by ordinary technicians in the field without creative labor are within the scope of the present invention.

For the content distribution of inclusions on the surface of large size metallic materials, because the area of the test sample is too large, on the one hand, the conventional test methods can't directly analyze it, and on the other hand, the indirect test methods (such as extreme value method) can only infer the content of the largest inclusions, the method can't give the results of all inclusion distribution. Some spectral analysis methods can characterize inclusions and their distribution information, but these methods use rough threshold to distinguish the signal of inclusions for acquirement of the intensity distribution of inclusions, thus obtaining the distribution method of inclusions, however, the methods cannot obtain the accurate actual distribution of inclusions.

The purpose of the invention is to provide a spark spectrometry for inclusions content distribution on the surface of large size metallic materials; the invention correlates the size information under scanning electron microscope with the inclusion signal data information of spectrometry of large-size metal samples to determine the relationship between the size and intensity of inclusions, thus obtaining the content distribution information of large size samples, which solves the problem of content distribution analysis of large size inclusions.

In order to make the above objects, features and advantages of the present invention more obvious and understandable, the present invention will be explained in further detail below with reference to the drawings and detailed description.

Figure 1:
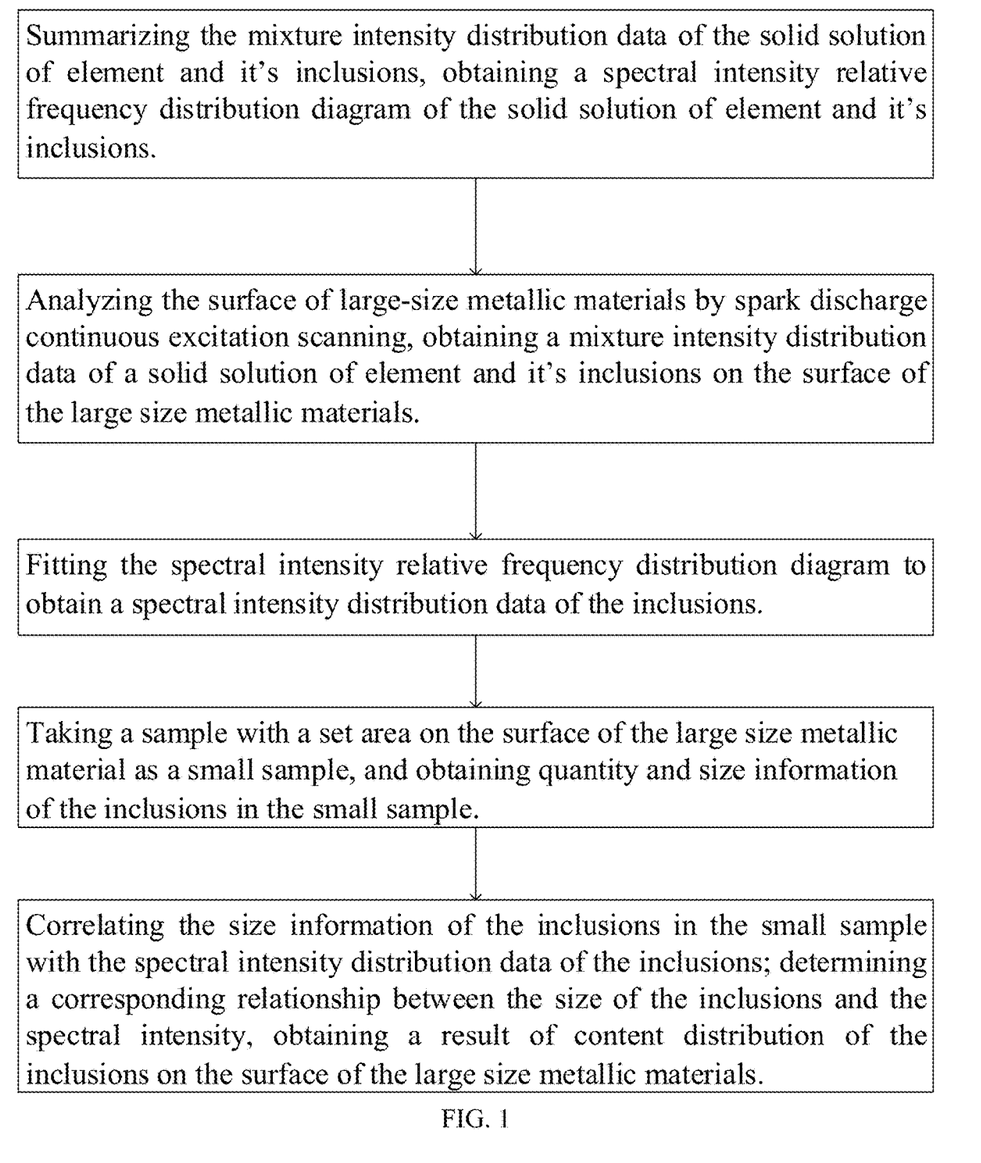
FIG. 1 illustrates a flow chart of the spark spectrometry analysis method for the content distribution of inclusions on the surface of large-size metal materials according to the present invention.
Figure 2:
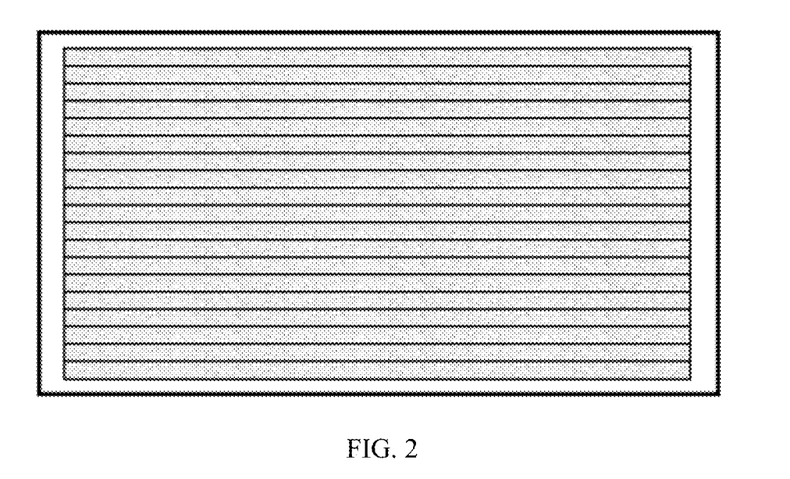
FIG. 2 illustrates a scanning schematic diagram of spark spectrometry.
Figure 3:
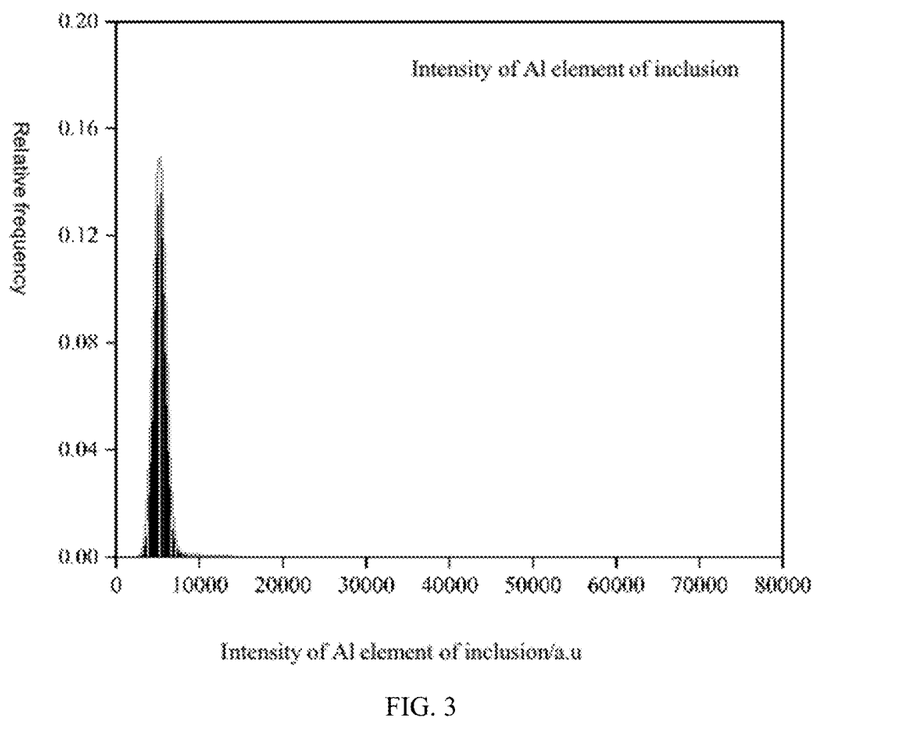
FIG. 3 illustrates a schematic diagram of relative frequency intensity distribution of solid solution of Al element and Al inclusion intensity distribution in the embodiment of the present invention.
Figure 4:
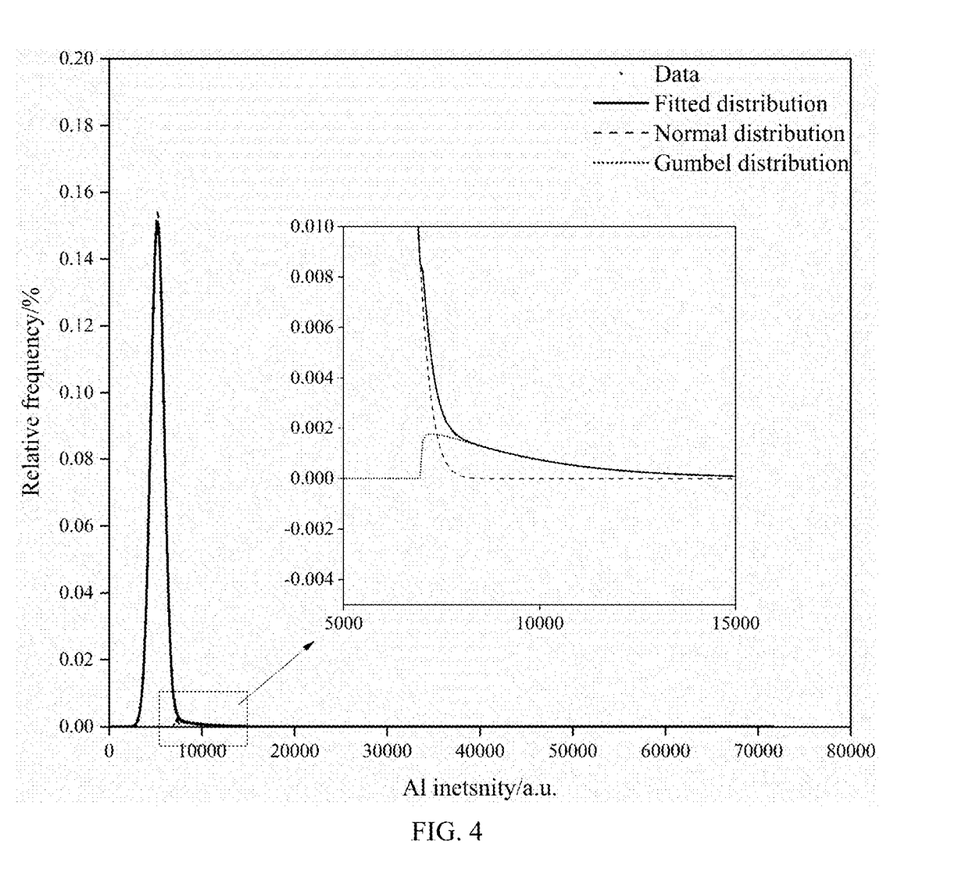
FIG. 4 illustrates a fitting diagram of the intensity frequency distribution of Al element in the embodiment of the present invention.
Figure 5:
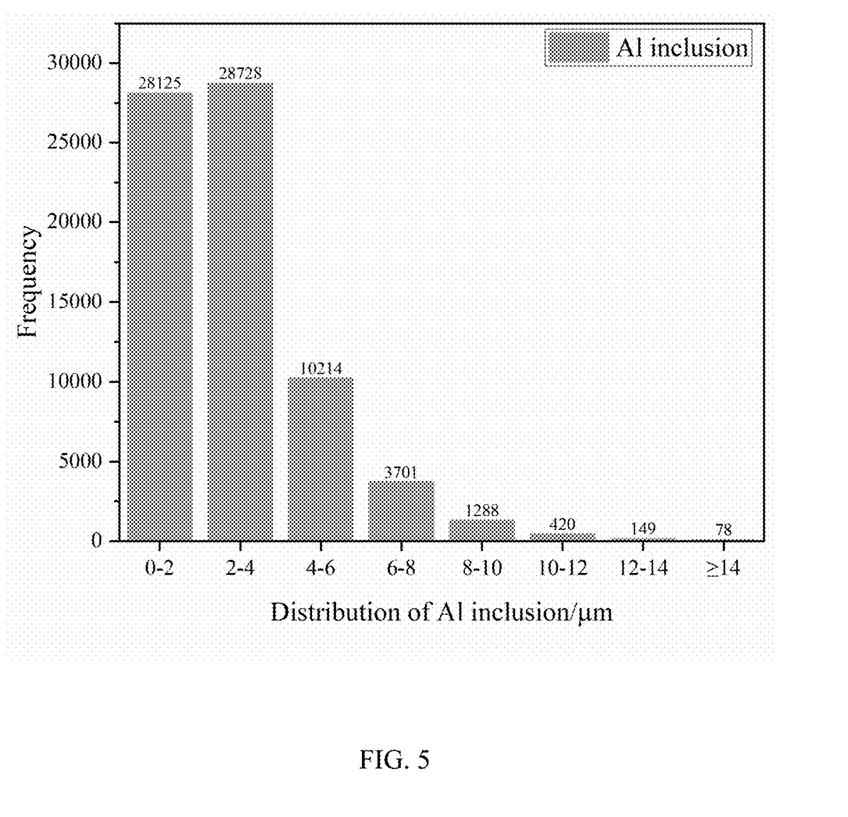
FIG. 5 illustrates the results of the content distribution of Al inclusions in the embodiment of the present invention.

As FIG. 1 illustrates, this invention provides a spark spectrometry for inclusions content distribution on the surface of large size metallic materials, comprising the following steps:

analyzing the surface of large-size metallic materials by spark discharge continuous excitation scanning, obtaining a mixture intensity distribution data of a solid solution of element and it's inclusions on the surface of the large size metallic materials;

summarizing the mixture intensity distribution data of the solid solution of element and it's inclusions, obtaining a spectral intensity relative frequency distribution diagram of the solid solution of element and it's inclusions;

the mixture intensity distribution data of solid solution and inclusions are summarized to obtain the relative frequency of intensity distribution diagram of solid solution and inclusions; taking A1 element as an example, the relative frequency intensity distribution diagram of solid solution of A1 element and inclusion intensity distribution are shown in FIG. 3. It can be seen from the Figure that the relative frequency distribution of the whole intensity is right-skewed distribution, and the main reason for right-skewed distribution is that the intensity of aluminum inclusions exceeds the intensity of the solid solution of aluminum;

fitting the spectral intensity relative frequency distribution diagram to obtain a spectral intensity distribution data of the inclusions; taking A1 element as an example, the fitting diagram of A1 element intensity frequency distribution is shown in FIG. 4. The main peak is mainly the spectral intensity relative frequency distribution of solid solution of A1, and the right-skewed distribution or trailing part is mainly the intensity relative frequency distribution of A1 inclusion;

taking a sample with a pre-set area on the surface of the large size metallic material as a small sample, and obtaining quantity and a size information of the inclusions in the small sample;

correlating the size information of the inclusions in the small sample with the spectral intensity distribution data of the inclusions, determining the corresponding relationship between the size of the inclusions and the spectral intensity, obtaining the content distribution result of the inclusions on the surface of large size metallic materials, taking A1 as an example, the content distribution results of A1 inclusions are shown in FIG. 5. The sizes of A1 inclusions in the whole large-size sample are concentrated in the range of 0-2 μm and 2-4 μm, and the number of A1 inclusions larger than 14 μm is the least;

Wherein, analyzing the surface of large-size metallic materials by spark discharge continuous excitation scanning, obtaining a mixture distribution data of a solid solution of elements of inclusions and a spectral intensity of inclusions on the surface of the large size metallic materials, comprising: FIG. 2 is the scanning schematic diagram of spark spectrometry, the gray part is the continuous scanning trace, and the surface of large size metallic materials is continuously scanned and analyzed by spark spectrometry; first, placing a scanning probe at the leftmost position of the upper end of the large size metallic materials in the Y direction, and carrying out spark discharge scan from left to right along the X direction, after scanning the first line, placing the scanning probe at the leftmost position of the second line at the upper end of the large size metallic materials in Y direction, next, completing the second line of scanning from left to right until all the lines of the large size metallic materials are scanned from top to bottom, obtaining the mixture intensity distribution data of solid solution of element and it's inclusions on the surface of the large size metallic materials.

The common spark spectrometry uses multi-channel element spark excitation source to excite the sample, and the scanning position is accurately positioned, and each position (X, Y) obtains the corresponding multi-channel element spark emission spectral intensity I (X, Y). The measured element spark emission intensities I (X, Y) are arranged from small to large, and 256 intensity signal distributions are obtained with corresponding class interval. For inclusion signals in elements, the spectral intensity signal distribution is a tail distribution on the right side of the normal distribution, that is, the average value is not in the center of the distribution map. The main reason for the tail distribution is that the non-solid solution part of elements appear as the rich aggregate of the inclusion elements in the spectral signal after the inclusion is formed, which results in the high spectral signal intensity of the inclusion element, a larger size and area of inclusions, resulting in a higher enrichment degree of inclusions, thus making a greater corresponding spectral intensity.

This invention provides a spark spectrometry for inclusions content distribution on the surface of large size metallic materials. First, a spectrum analysis system is configured, and the excitation source is a solid-state pulse discharge light source. The configuration optical system can be Rowland circle or other optical systems, and the light intensity acquisition component can be photomultiplier tube, CCD detector or CMOS detector. X- and Y-direction precision transmission devices are adopted. The common spark spectrometry uses multi-channel element spark excitation source to excite the sample, and the scanning position is accurately positioned, and each position (X, Y) obtains the corresponding multi-channel element spark emission spectral intensity I (X, Y). The measured elements' spark emission intensities I (X, Y) are arranged from small to large, and 256 intensity signal distributions are obtained with corresponding class interval. Mathematical fitting the histogram of intensity distribution frequency of inclusion elements to obtain the relative frequency distribution diagram of inclusion intensity.

In the embodiment, fitting the spectral intensity relative frequency distribution graph to obtain the spectral intensity distribution data of inclusions, comprising:

Carrying out peak fitting process on the spectral intensity relative frequency distribution diagram by normal distribution and Gumbel distribution to obtain the normal distribution diagram of the solid solution part of the left main peak and the Gumbel distribution diagram of the inclusions of the right peak tailing; wherein, the main peak on the left side is the intensity distribution of the solid solution part of the element, which presents a Gaussian function distribution, and the function expression is:

$$f(x) = \frac{1}{\sqrt{2\pi}\sigma} \exp\left(-\frac{(x-\mu)^2}{2\sigma^2}\right);$$

wherein, μ is the expected value of the intensity average and σ is expected value of the standard deviation;

The peak tailing on the right side represents the intensity distribution of inclusions, which shows Gumbel distribution, and the function expression is:

$$f(x) = \frac{1}{\delta}\left[\exp\left(-\frac{x-\lambda}{\delta}\right)\right] \times \exp\left[-\exp\left(-\frac{x-\lambda}{\delta}\right)\right];$$

wherein, λ is the positioning parameter and δ is the scale parameter.

After fitting, the functional distribution expression of the total strength (including solid solution and inclusions) of this element is:

$$f(x) = \frac{1}{\sqrt{2\pi}\sigma} \exp\left(-\frac{(x-\mu)^2}{2\sigma^2}\right) + \frac{1}{\delta}\left[\exp\left(-\frac{x-\lambda}{\delta}\right)\right] \times \exp\left[-\exp\left(-\frac{x-\lambda}{\delta}\right)\right];$$

Spectral intensity distribution data of the inclusions is obtained based on the Gumbel extreme value distribution diagram of the inclusions at the right trailing peak.

Peak tailing function is the frequency distribution function of inclusion intensity, and its intensity and relative frequency are distributed in the area of diagram where shows intensity, namely, it is the threshold value of inclusion intensity, therefore, the peak tailing function clearly distinguishes the intensity-relative frequency of the solid solution from the intensity-relative frequency of the inclusions. Thus accurately distinguishing the solid solution intensity-relative frequency distribution and inclusion intensity-relative frequency distribution of the element.

According to the invention, the distribution of spark intensity is decomposed into normal distribution and Gumbel distribution by using peak-fitting mathematical model of the relative frequency and intensity of the inclusion elements. However, it is not limited to Gumbel distribution, and it can also be applied to other extreme value distributions like Generalized Pareto Distribution.

According to the standard GB/T 40281-2021 "Determination of nonmetallic inclusions in steel-extreme value analysis method", a small part of samples (scanning area is $S_{small}$) is taken from large size metallic materials (scanning area is $S_{large}$).

In embodiment, taking the sample with the pre-set area on the surface of the large size metallic materials as the small sample, comprising processes as follows:
obtaining the area of the surface of the large size metallic materials, which is expressed as $S_{large}$;
obtaining the pre-set area of the small sample, which is expressed as $S_{small}$;
the surface area of large size metallic materials and the pre-set area of the small sample, satisfying the following relationship:

$$T = S_{large}/S_{small}$$

wherein, T is within the range of 100~10000.

The estimated maximum inclusion probability is 99%~99.99%, the value of small sample S can be determined, according to the actual scanning area $S_{large}$ and the value of T.

In embodiment, taking the sample with the pre-set area on the surface of the large size metallic materials as the small sample, and obtaining the quantity and size information of the inclusions in the small sample, comprising processes as follows: grinding and polishing a sample with a pre-set area on the surface of a large size metallic materials as a small sample, placing the small sample under a scanning electron microscope, and identifying and quantitatively detecting inclusions larger than 1 μm on the surface of the small sample, at the same time, aluminum foil is introduced to the edge of the small sample to correct the gray threshold of the electron microscope picture, confirming the recognition brightness threshold of the inclusions. When the brightness of the particles observed by scanning electron microscope is less than the brightness threshold, the particles are judged as inclusions, and the energy spectrum analysis is carried out to record and save a quantity and size information of inclusions, and the quantity and size information of the largest inclusions is recorded as the first data.

Further, taking the sample with the pre-set area on the surface of the large size metallic materials as the small sample, and obtaining the quantity and size information of the inclusions in the small sample, comprising processes as follows: taking a sample with a pre-set area on the surface of the large size metallic materials, re-preparing the sample, grinding and polishing the re-prepared sample, and placing it under a scanning electron microscope again to obtain a size information of the largest inclusions, and recording it as the second data; repeating the same process described in the previous sentence, in order to obtain the size information of the largest inclusions and record it as the third data; repeating the same process until 24 groups of data are recorded; according to the standard GB/T 40281-2021 "Determination of Non-metallic Inclusions in Steel-Extreme Value Analysis Method", the size information of the largest inclusion of this element in the 24 groups is collected, in order to calculate the area $S_{max}$ of this element of inclusion, corresponding to the size of the largest inclusion formed by this inclusion element in $S_{large}$. At this time, the calculated size of the largest element of inclusion should correspond to the maximum intensity $A_{max}$ in Gumbel distribution.

In the embodiment, correlating the size information of the inclusions in the small sample with the spectral intensity distribution data of the inclusions; determining a corresponding relationship between the size of the inclusions and the spectral intensity, obtaining a result of content distribution of the inclusions on the surface of the large size metallic materials, comprising:
the size information of inclusions are classified and counted under scanning electron microscope in the form of equivalent circle, for example, 0-2 μm, 2-4 μm, 4-6 μm, 6-8 μm, 8-10 μm, 10-12 μm, 12-14 μm, . . . , in order to obtain statistical frequencies of each group with the interval of 2 μm;

The spectral intensity distribution data of inclusions are divided into the same groups based on the statistical frequency of 2 μm group spacing under scanning electron microscope, and the average size and average intensity of each group are recorded as D1, D2, D3, D4 and A1, A2, A3, A4 respectively.

According to the relationship between the average intensity of each group or the maximum intensity and the average or largest size of inclusions obtained at grouped frequency, the intensity and inclusion size correction curve is drawn. Specifically, in some literatures on park spectrometry of inclusions, the intensity and size of inclusions are positively correlated with parabola. According to the data of points $(D_1, A_1)$, $(D_2, A_2)$, $(D_3, A_3)$, $(D_4, A_4)$ and $(D_{max}, A_{max})$, a calibration curve can be drawn to obtain $A=aD^2+bD+C$;

then, according to the intensity and inclusion size correction curve, the intensity-relative frequency spectrogram is converted into the inclusion size-frequency spectrum, multiplied the inclusion size-frequency spectrum by the total spectral intensity of inclusion elements to obtain the inclusion size distribution diagram, and the distribution result of inclusion content is obtained by the set class intervals.

This invention provides a spark spectrometry for inclusions content distribution on the surface of large size metallic materials, which analyzes the surface of metal materials by spark discharge continuous excitation scanning to obtain the solid solution of elements of inclusions and the spectral intensity of inclusions on the surface of the large size metallic materials; the obtained data are summarized to obtain the relative frequency distribution diagram of solid solution and inclusion intensity mixing of an element. Fitting the distribution diagram, separating the solid solution intensity signal of elements from the inclusion intensity signal, thereby realizing the separation of the inclusion intensity signal and the solid solution signal. A small part of samples (scanning area is $S_{small}$) is taken from large size metallic materials (scanning area is $S_{large}$).

According to the requirements of inclusions detection, the surface samples are prepared, and the small samples are placed under the scanning electron microscope. According to the analysis of the scanning electron microscope, the number and size information of inclusions in the small samples are summarized. The size information of inclusions under scanning electron microscope is correlated with the intensity distribution of inclusions scanned by spark spectrometry on large sized metal sample, and the corresponding relationship between the size and intensity of inclusions is determined, so as to obtain the size distribution information of inclusions in large size metal samples, thus solving the problem of content distribution analysis of large size inclusions.

In this invention, specific examples are used to explain the principle and implementation of the present invention, and the explanations of the above embodiments are only used to help understand the method and core ideas of the present invention; At the same time, according to the idea of the present invention, there will be some changes in the specific implementation and application scope for those of ordinary skill in the field. To sum up, the contents of this specification should not be construed as limiting the present invention.

What is claimed is:

1. A method of spark spectrometry for inclusions content distribution on the surface of large size metallic materials, comprising the following steps:

analyzing the surface of large-size metallic materials by spark discharge continuous excitation scanning, obtaining a mixture intensity distribution data of a solid solution of element and its inclusions on the surface of the large size metallic materials;

summarizing the mixture intensity distribution data of the solid solution of element and its inclusions, obtaining a spectral intensity relative frequency distribution diagram of the solid solution of element and its inclusions;

fitting the spectral intensity relative frequency distribution diagram to obtain a spectral intensity distribution data of the inclusions;

taking a sample with a pre-set area on the surface of the large size metallic materials as a small sample, and obtaining quantity and a size information of the inclusions in the small sample;

correlating the size information of the inclusions in the small sample with the spectral intensity distribution data of the inclusions; determining a corresponding relationship between the size of the inclusions and the spectral intensity, obtaining a result of content distribution of the inclusions on the surface of the large size metallic materials.

2. The method of spark spectrometry for inclusions content distribution on the surface of large size metallic materials as claimed in claim 1, the step of analyzing the surface of the large size metallic materials by the spark discharge continuous excitation scanning, obtaining the mixture distribution data of solid solution of elements of inclusions and the spectral intensity of inclusions on the surface of the large size metallic materials, comprising processes as follows: first, placing a scanning probe at the leftmost position of the upper end of the large size metallic materials in the Y direction, and carrying out spark discharge scan from left to right along the X direction, after scanning the first line, placing the scanning probe at the leftmost position of the second line at the upper end of the large size metallic materials in Y direction, next, completing the second line of scanning from left to right until all the lines of the large size metallic materials are scanned from top to bottom, obtaining the mixture distribution data of solid solution of elements of inclusions and the spectral intensity of inclusions on the surface of the large size metallic materials.

3. The method of spark spectrometry for inclusions content distribution on the surface of large size metallic materials as claimed in claim 1, the step of fitting the spectral intensity relative frequency distribution diagram to obtain the spectral intensity distribution data of the inclusions, comprising processes as follows:

carrying out peak fitting processing on the spectral intensity relative frequency distribution diagram by normal distribution and Gumbel distribution to obtain the normal distribution diagram of the solid solution part of the left main peak and the Gumbel distribution diagram of the inclusions of the right peak tailing;

obtaining the spectral intensity distribution data of the inclusions based on the Gumbel distribution diagram of the inclusions at the right peak tailing.

4. The method of spark spectrometry for inclusions content distribution on the surface of large size metallic materials as claimed in claim 1, the step of taking the sample with the pre-set area on the surface of the large size metallic materials as the small sample, comprising processes as follows:

obtaining the area of the surface of the large size metallic materials, which is expressed as $S_{large}$;

obtaining the pre-set area of the small sample, which is expressed as $S_{small}$;

the surface area of large size metallic materials and the pre-set area of the small sample, satisfying the following relationship:

$$T=S_{large}/S_{small};$$

wherein, T is within the range of 100~10000.

5. The method of spark spectrometry for inclusions content distribution on the surface of large size metallic materials as claimed in claim 1, the step of taking the sample with the pre-set area on the surface of the large size metallic materials as a small sample, and obtaining the quantity and size information of the inclusions in the small sample, comprising processes as follows:

grinding and polishing a sample with a pre-set area on the surface of a large size metallic materials as the small sample, placing the small sample under a scanning electron microscope, identifying and quantitatively detecting inclusions larger than 1 μm on the surface of small samples, at the same time, aluminum foil is introduced to the edge of the small sample to correct the gray threshold of the electron microscope picture, confirming a recognition brightness threshold of the inclusions;

when the brightness of the particles observed by scanning electron microscope is less than the brightness threshold, the particles are judged as inclusions, and energy spectrum analysis is carried out to record and save a quantity and size information of inclusions, and the quantity and size information of the largest inclusions is recorded as first data.

6. The method of spark spectrometry for inclusions content distribution on the surface of large size metallic materials as claimed in claim 5, the step of taking the sample with the pre-set area on the surface of the large size metallic materials as the small sample, and obtaining the quantity and size information of the inclusions in the small sample, comprising processes as follows:

taking the sample with the pre-set area on the surface of the large size metallic materials a second time, re-preparing the sample, grinding and polishing the re-prepared sample to obtain a small sample, and placing it under a scanning electron microscope again to obtain the size information of the largest inclusions, and recording it as second data;

repeating the same process of sampling, re-preparing sample, grinding and polishing the re-prepared sample, in order to obtain the size information of the largest inclusions and record it as third data;

repeating the same process until 24 groups of data are recorded; and based on extreme value analysis, calculating the size of the largest inclusions of elements on the surface of the large size metallic materials, the calculated size corresponds to a maximum intensity signal in the spectral intensity distribution data of inclusions.

7. The method of spark spectrometry for inclusions content distribution on the surface of large size metallic materials as claimed in claim 6, the step of correlating the size information of the inclusions in the small sample with the spectral intensity distribution data of the inclusions; determining the corresponding relationship between the size of inclusions and spectral intensity, obtaining the result of content distribution of the inclusions on the surface of large size metallic materials, comprising processes as follows:

classifying and counting the size information of the inclusions under a scanning electron microscope, obtaining a statistical frequency of each class with a class interval of 2 μm;

the spectral intensity distribution data of the inclusions are divided into the same class based on the statistical frequency of the 2 μm class interval under scanning electron microscope, obtaining the average size and average intensity of each class;

drawing a calibration curve of areas to intensity according to the relationship of the average intensity of each class and the maximum intensity of all classes with the average size and maximum size of the inclusions obtained under the class frequency process; and according to a calibration curve of intensity to size converting the intensity-relative frequency spectrum into a size-frequency spectrum of the inclusions, multiplying total numbers of spectral intensity signal of inclusions to obtain an inclusions size distribution graph, setting the class interval to distinguish each class, thus obtaining the result of inclusions content distribution.

* * * * *